(12) United States Patent
Ciavarella et al.

(10) Patent No.: US 8,950,632 B2
(45) Date of Patent: Feb. 10, 2015

(54) WEARABLE DISPENSER

(75) Inventors: Nick E. Ciavarella, Seven Hills, OH (US); Matthew I. Archer, Aurora, OH (US)

(73) Assignee: Gojo Industries, Inc., Akron, OH (US)

( * ) Notice: Subject to any disclaimer, the term of this patent is extended or adjusted under 35 U.S.C. 154(b) by 398 days.

(21) Appl. No.: 13/309,928

(22) Filed: Dec. 2, 2011

(65) Prior Publication Data

US 2012/0138637 A1 Jun. 7, 2012

Related U.S. Application Data

(60) Provisional application No. 61/418,921, filed on Dec. 2, 2010.

(51) Int. Cl.
| | |
|---|---|
| *B67D 7/84* | (2010.01) |
| *A61L 2/18* | (2006.01) |
| *A44C 5/00* | (2006.01) |
| *A44C 15/00* | (2006.01) |
| *A61L 2/22* | (2006.01) |
| *A61L 9/12* | (2006.01) |
| *A61L 9/14* | (2006.01) |
| *B05B 11/00* | (2006.01) |

(52) U.S. Cl.
CPC .................. *A61L 2/18* (2013.01); *A44C 5/0023* (2013.01); *A44C 15/002* (2013.01); *A61L 2/22* (2013.01); *A61L 9/12* (2013.01); *A61L 9/14* (2013.01); *B05B 11/30* (2013.01); *B05B 11/0027* (2013.01); *B05B 11/0037* (2013.01); *B05B 11/0048* (2013.01); *A61L 2202/15* (2013.01)
USPC ...................... 222/175; 224/148.2; 224/148.4; 224/219

(58) Field of Classification Search
CPC ...... A44C 5/0023; A44C 15/002; A61L 2/18; A61L 2/22; A61L 9/12; A61L 9/14; A61L 2202/15; B05B 11/0027; B05B 11/0037; B05B 11/0048
USPC ................. 222/175; 224/148.1, 148.2, 148.4, 224/148.5, 148.7, 219, 222
See application file for complete search history.

(56) References Cited

U.S. PATENT DOCUMENTS

| | | |
|---|---|---|
| 692,089 A | 1/1902 | Swisher et al. |
| 2,235,350 A | 3/1941 | Anderson et al. |
| 4,176,772 A | 12/1979 | Danon |
| 5,358,144 A | 10/1994 | Mock |
| 5,957,347 A | 9/1999 | White et al. |

(Continued)

FOREIGN PATENT DOCUMENTS

| | | | |
|---|---|---|---|
| DE | 202006009161 | 10/2006 | |
| GB | 204657 | * 10/1923 | ........... A44C 15/002 |

(Continued)

*Primary Examiner* — J. Casimer Jacyna
(74) *Attorney, Agent, or Firm* — Renner Kenner Greive Bobak Taylor & Weber (57) ABSTRACT

A wearable dispenser is provided having an elongate body having a first end and a second end and extending from the first end to the second end in an arc forming at least a portion of an ellipse, oval or circle and extending through greater than 180 degrees so as to fit over a wrist. A product is retained interiorly of the body, and a pump assembly fluidly communicates with the product in the body. The pump assembly includes a movable dispensing tip that, upon reciprocal movement, dispenses a dose of product from the pump assembly and draws another dose of product into the pump assembly.

7 Claims, 6 Drawing Sheets

(56) References Cited

U.S. PATENT DOCUMENTS

| | | | |
|---|---|---|---|
| 6,126,041 | A | 10/2000 | DiTomasso et al. |
| 7,135,011 | B2 | 11/2006 | Powers et al. |
| 7,316,332 | B2 | 1/2008 | Powers et al. |
| 7,766,193 | B2 | 8/2010 | Stollmann et al. |
| 8,708,194 | B2 * | 4/2014 | Pascatore .................. 222/1 |
| 2011/0155765 | A1 * | 6/2011 | Properzi ................ 222/175 |

FOREIGN PATENT DOCUMENTS

| | | | | |
|---|---|---|---|---|
| GB | 2235861 | * | 3/1991 | ......... A44C 15/002 |
| KR | 20080107843 | | 12/2008 | |
| WO | 2004052425 | | 6/2004 | |
| WO | 2007035366 | | 3/2007 | |
| WO | 2009088964 | | 7/2009 | |

* cited by examiner

WEARABLE DISPENSER

CROSS-REFERENCE TO RELATED APPLICATION

This application claims priority from U.S. provisional patent application Ser. No. 61/418,921 filed on Dec. 2, 2010, which is incorporated herein by reference in its entirety.

FIELD OF THE INVENTION

The present invention relates to dispensers. More particularly, the present invention relates to dispensers that may be worn by a user. Virtually any desired flowable product may be dispensed by these dispensers, and hand hygiene products such as sanitizers are of specific interest.

BACKGROUND OF THE INVENTION

The use of hand sanitizers has become so common that there is a significant portion of the population that always keeps hand sanitizers at a nearby location, be it in the drawer of a desk at work or, even more readily available in a pocket or purse. Small, readily portable sanitizer dispensers are provided specifically so that the sanitizer can be stored in a manner such that it is always readily available. The dispensers most commonly employed for these purposes are simply small squeeze bottles closed off by a cap having a dispenser aperture through which the product is dispensed. The small, flexible bottle is typically inverted so that the sanitizer fills the volume near the dispensing aperture while air in the container moves upwardly toward what was previously the bottom of the container. The container is then squeezed so that a desired amount of product is forced out of the dispensing aperture and onto one's hand, at which time it can be used by rubbing the hands together to distribute the sanitizer. These dispensers are practical and popular, but they serve only the purpose of acting as a dispenser, and they are not as readily accessible as they could be because, in order to be used, they must still be retrieved from a desk drawer, pocket or purse or elsewhere, depending upon where they are stored.

The art of sanitizer dispensers can be improved upon by providing dispensers that are even more readily accessible for use than those dispensers of the prior art. The art of sanitizer dispensing may also be improved by the provision of a dispenser that serves more than the function of being a dispenser, i.e., serves a dual purpose. Although the present application focuses particularly upon sanitizer dispensers, it should be appreciated that the concepts of the present invention can be applied to dispense any flowable product, such that the invention is not limited to or by a specific product to be dispensed. By way of particular, non-limiting example, concepts of the present invention could be applied to provide dispensing devices for dispensing bug repellent, sunblock, hand/body lotion or soap, breath freshener and the like.

SUMMARY OF THE INVENTION

In general, this invention provides wearable dispenser comprising an elongate body having a first end and a second end and extending from the first end to the second end in an arc forming at least a portion of an ellipse, oval or circle and extending through greater than 180 degrees so as to fit over a wrist. A product is retained interiorly of the body, and a pump assembly fluidly communicates with the product in the body. The pump assembly includes a movable dispensing tip that, upon reciprocal movement, dispenses a dose of product from the pump assembly and draws another dose of product into the pump assembly.

In one or more embodiments, the second end of the body provides a connection space, wherein the body is formed of a flexible material, wherein the body extends from the first end to the second end in an arc forming at least one ellipse, oval or circle, and wherein at least a portion of the movable dispensing tip of the pump assembly is received in the connection space.

In one or more embodiments, the wearable dispenser further comprises a catch at the second end of the body, wherein the body is formed of a flexible material, wherein the body extends from the first end to the second end in an arc forming at least one ellipse, oval or circle, and wherein at least a portion of the movable dispensing tip of the pump assembly is received in the catch.

In one or more embodiments, the body is formed of a resilient material that maintains the arc extending through greater than 180 degrees, at rest, the resilient material yielding to forces in placing the dispenser on or removing the dispenser from a wrist.

In one or more embodiments, the body extends from the first end to the second end in an arc forming at least one ellipse, oval or circle.

In one or more embodiments, the body defines a product space, the product space retaining the product, and, upon reciprocal movement, the movable dispensing tip dispenses a dose of product from the pump assembly and draws another dose of product into the pump assembly from the product space. In one or more embodiments, the product space is vented such that air replaces the doses of product drawn into the product space.

In one or more embodiments, the product is retained in a collapsible container extending interiorly of the body. In one or more embodiments, the pump assembly and the collapsible container form a refill unit removable from the body. In one or more embodiments, the body is vented such that air may enter between the body and the collapsible container. In one or more embodiments, the collapsible container is a bellows chamber. In one or more embodiments, the collapsible container is a collapsible bag.

In one or more embodiments, the body defines a product space retaining the product, the wearable dispenser further comprising a plug follower inside the product space, wherein, upon reciprocal movement, the movable dispensing tip dispenses a dose of product from the pump assembly and draws another dose of product into the pump assembly from the product space, the vacuum created thereby drawing the plug follower toward the pump assembly, the plug follower keeping the product isolated from air.

In one or more embodiments, the pump assembly includes a base secured to the body, and a rotating cap, the movable dispensing tip extending from the rotating cap. In one or more embodiments, the movable dispensing tip extends from the rotating cap such that it extends perpendicularly to the axis of the body.

DETAILED DESCRIPTION OF ILLUSTRATIVE EMBODIMENTS

Figure 1:
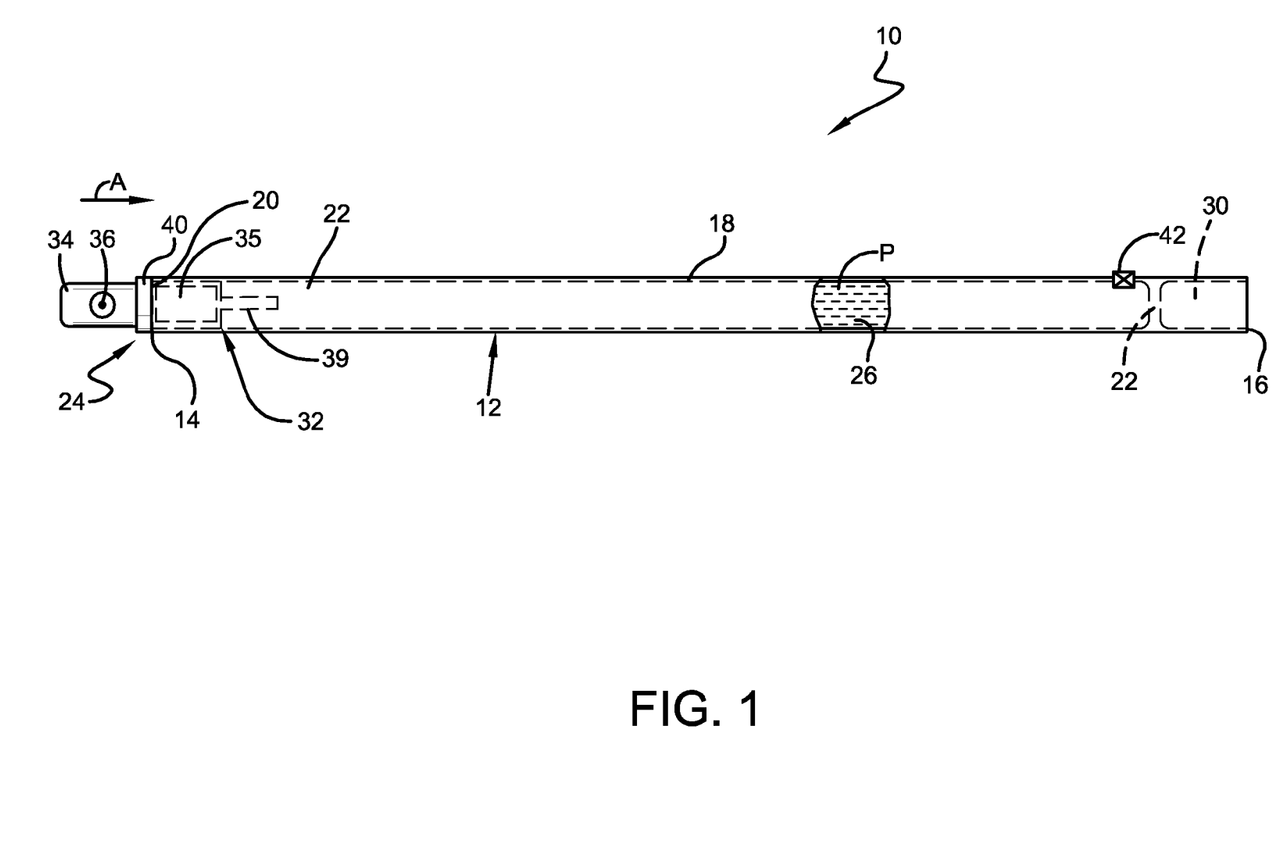
FIG. 1 is a side elevational view of a dispensing device in accordance with this invention.
Figure 2:
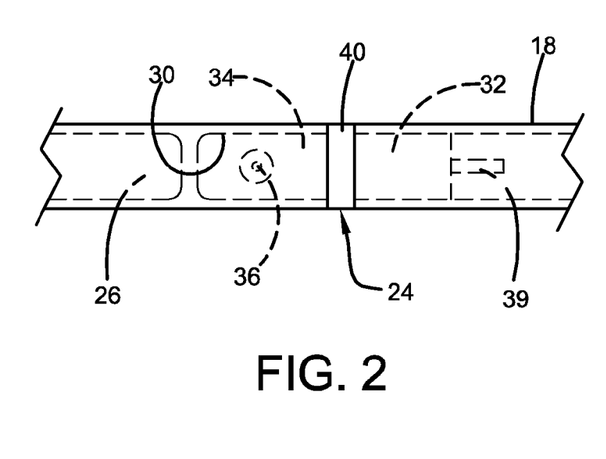
FIG. 2 is a side elevational view showing the mating of a movable dispensing tip at a first end of the dispenser mating with a connection space at a second end of the dispenser.
Figure 3:
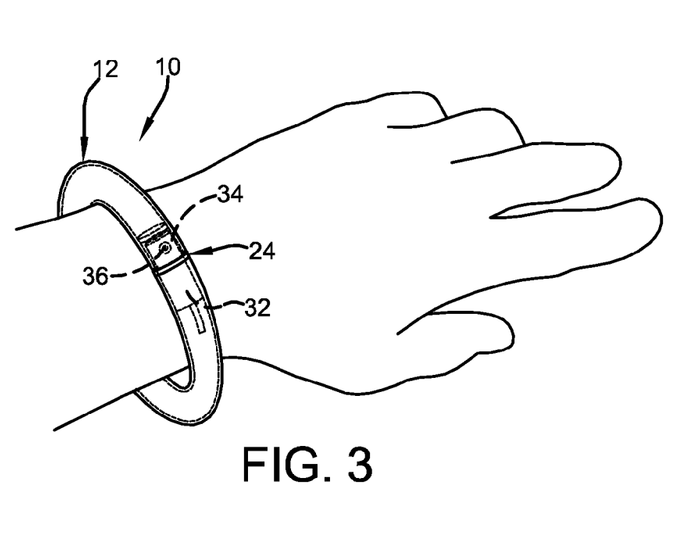
FIG. 3 is a perspective view showing the dispenser of FIGS. 1 and 2 being worn on a user's wrist.

Referring to FIGS. 1-3, a first embodiment of a wearable dispenser in accordance with this invention is shown and designated by the numeral 10. The dispenser 10 includes a body 12 of a length that extends axially from a first end 14 to a second end 16. Though this embodiment shows a body 12 that is cylindrical in cross section, having a cylindrically-shaped sidewall 18, it will be appreciated that practice of this invention does not depend thereon, and other cross-sectional shapes can be employed, as may be desired for a given aesthetic or functional effect.

The body 12 is formed of one or more sidewalls 18 and is thereby generally hollow as it extends from an opening 20 at the first end 14 to the second end 16. However the body 12 includes a partition 22, extending proximate to and recessed from second end 16. A pump assembly 24 fits within the opening 20 defined at first end 14 to thereby close off and define a product space 26 between the partition 22 and the base wall 28 of the pump assembly 24. As best seen at the portion of wall 18 removed in FIG. 1, this product space 26 holds a volume of product P that will be dispensed upon proper usage of the dispenser 10. A connection space 30 is defined between the partition 22 and the second end 16.

In the particular structure shown, the pump assembly 24 includes a housing 32 and a movable dispensing tip 34, and the housing 32 fits within the opening 20 to close off the product space 26. However, it will be appreciated that the housing 32 does not have to fit with the opening 20, and could instead simply cover the opening 20 to fluidly communicate with the product P in the product space 26. For example, the bottom end of housing 32 could be shaped to abut and be adhered (or otherwise secured) to the first end 14, over the opening 20, so that the pump assembly 24 closes off the product space 26, but without the housing 32 fitting into the product space 26. When the housing 32 is designed to fit within the opening 20, it can be friction fit therein, or held by and adhesive, or secured by mating threads on the interior surface of the body 12 and the exterior surface of the housing 32.

As generally known, the movable dispensing tip 34 is pressed in the direction of arrow A to dispense a dose of product from the dispenser 10 at the outlet 36 of the movable dispensing tip 34. More particularly, the housing 32 provides a product chamber 35, and, when the movable dispensing tip 34 is pressed in the direction of arrow A, the volume of the product chamber 35 is reduced and its contents are expelled therefrom, through an outlet path toward the outlet 36. Depending upon the volume of the outlet path, the contents may be dispensed at the outlet 36 or may instead cause a previously expelled dose to be dispensed at the outlet 36.

The movable dispensing tip 34 is usually under a biasing influence to return it to its original position, and, when it moves in the direction opposite arrow A, the volume of the product chamber 35 is increased and its contents replenished. The product chamber and flow path or paths in the pump assembly 24 are appropriately structured and in operative connection with valve structures such that the reciprocal movement of the movable dispensing tip 34 dispenses a dose of product P from the product chamber 35 and draws a dose of product P into the product chamber 35. The product chamber 35 fluidly communicates with the product space 26, and the increase in the volume of the product chamber 35 creates a vacuum that draws in product P from the product space 26. A dip tube such as that at numeral 39 could be employed to provide communication between the contents of the product space 26 and the product chamber 35. This is all well known in the art of dispensers, and various structures can be employed. For less viscous product (low viscosity sanitizer, bug spray, breath freshener), the pump assembly may provide a pump that doses out the product as a simple stream or as a spray or as a mist, and, for more viscous product (lotions, gel-type sanitizers), the pump assembly may provide a pump that doses out the product a simple stream. The pump may also be chosen such that the product is dispensed as a foam, and such foam pumps are well know.

Referring now to FIG. 2, it can be seen that the movable dispensing tip 34 is provided with a cross sectional shape such that it can be inserted into the connection space 30 to create a friction fit between the outer surface of the movable dispensing tip 34 and the inner surface of the walls defining the connection space 30. In this embodiment, the housing 32 of the pump assembly 24 is similarly shaped with a cross section that can be inserted into the opening 20 of the first end 14 to create a friction fit between the pump assembly 24 and the body 12 at the inner surface of the wall or walls defining the product space 26. To assist in assembling the dispenser 10, the pump assembly 24 provides a collar 40 that abuts the first end 14 of the body 12, when the housing of the pump assembly 24 is fitted therein.

The body 12 is of a length suitable for wrapping around a user's wrist so that the dispenser 10 may be worn by the user similar to the manner in which a bracelet is worn. In this particular embodiment, as seen in FIG. 3, the length of the body 12 is selected to be of a suitably length for fitting properly on a user's wrist when the body 12 is bent to extend through an arc of 360 degrees so that the movable dispensing tip 34 is received in the connection space 30 and a circular bracelet is formed. In other embodiments, the length of body 12 could be chosen to extend though an arc of 720 degrees to form a bracelet that wraps twice around the writs. The body 12 can be chosen to bend and for a circle or an ellipse or oval, which are all suitable for fitting comfortably on a wrist, and the term "arc" as used herein should be appreciated as applying to ovals and ellipses as well as circles. The lengths could be chosen based on an average size suitable for wrists of various sizes, such as small, medium, large, extra large etc., and based on a desired number of windings for the bracelet formed thereby.

The pump assembly 24 may optionally be removably attached to the body 12. This would permit one to separate the pump assembly 24 from the body 12 in order to replenish the supply of product within the product space 26, thereafter reconnecting the pump assembly 24 with the body 12 to continue using the dispenser 10. A strong friction fit or a threaded or releasable snap-fit type engagement between the pump assembly 24 and the body 12 would be suitable for such a purpose. Other suitable engagements are taught herein with respect to other embodiments, but there suitability for this embodiment will be readily apparent.

The product carried by and dispensed by dispenser 10 can be any liquid, gel or lotion product that a user would like to dispense. Without limitation, such product may include sanitizers, bug repellants, sun blocks, hand/body lotion or soap, breath fresheners and the like.

The body 12 is preferably constructed of a material that is sufficiently flexible so that the body 12 may be deformed to bring the first end 14 into contact with the second end 16 (more particularly to place the movable dispensing tip 34 in the connection space 30) to form one or more loops that may fit around a user's wrist like a bracelet as described above. The body 12 should be sufficiently resilient to allow for repeated deformations between the linear and looped arrangements depicted in FIGS. 1 and 3, else the material might be compromised over time. Other characteristics of the body 12 may be chosen to suit a particular application. For example, the body 12 may be any color, may be transparent, may have a particular tactile feel, and so on.

Though various materials will be found to be suitable, in one or more embodiments, the body 12 is formed of a plastic material with elastomeric flex properties. Non-limiting examples include polyvinylchloride (PVC), vinyl, polyethylene (PE), silicone, polybutylene, and polyurethane. In one or more embodiments, the material of the body 12 is chosen to have a Durometer Shore A hardness in the range of from 10 to 60.

With this basic structure, the dispenser 10 may be worn by a user and used as needed. In particular, dispenser 10 may be formed into the looped arrangement and worn around the user's wrist, as shown in FIG. 3. When the user desires to use the dispenser 10, the movable dispensing tip 34 is removed from within the connection space 30 so that the dispenser 10 can be removed from the wrist and the movable dispensing tip 34 can be pressed to dispense product. Once the user has dispensed the liquid, the dispenser 10 may be reformed back into the loop arrangement and worn around the user's wrist.

Figure 4:
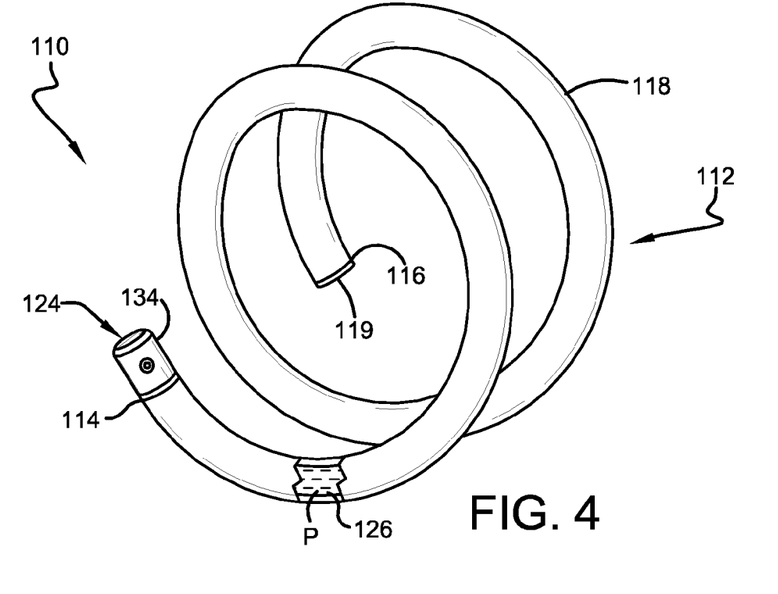
FIG. 4 is a perspective view of a second embodiment of a wearable dispenser in accordance with this invention.

Turning to FIG. 4, a second dispenser is shown and is indicated generally by the numeral 110. The dispenser 110 includes a body 112 extending from a first end 114 to a second end 116. In this embodiment, the body 112 is preformed to be generally coiled at rest so as to form one or more loops or portions of a loop, as shown (two loops are shown in this embodiment). Though this embodiment shows a body 112 that is cylindrical in cross section, having a cylindrically-shaped sidewall 118, it will be appreciated that practice of this invention does not depend thereon, and other cross-sectional shapes can be employed, as may be desired for a given aesthetic or functional effect. The body 112 is formed of one or more sidewalls 118 and is thereby generally hollow as it extends from the first end 114 to the second end 116, much like the embodiment of FIGS. 1 and 2. In the particular embodiment shown, the body 112 does not include a partition (as at partition 22 of the dispenser 10), because this embodiment is not intended to join end-to-end. Instead, the second end 116 is simply closed off as at cap 119. However, it should be appreciated that a partition could be employed (instead of a cap 119) to create a connection space, and an axial length of the pump assembly 124, particularly, the movable dispensing tip 134, could mate with the connection space substantially as described above with respect to the movable dispensing tip 34 and the connection space 30. That is the end-to-end connecting aspect of the embodiment of FIGS. 1-3 could readily be applied to this embodiment, as desired, and specific drawings and additional disclosures are unnecessary for the appreciation of this concept.

A pump assembly 124 fits within the open end defined at the first end 114 to thereby close off and define a product space 126 holding product P inside of the body 112. The pump assembly 124 can be fitted to the body 112 in any manner as described above with respect to the mating of the pump assembly 24 and the body 12. Pressing on the movable dispensing tip 134 of the pump assembly 124 will cause product to be dispensed, while releasing the movable dispensing tip 134 will cause product to be drawn into the pump assembly for later dispensing.

The body 112 is preferably constructed of a generally pliable material that is able to retain an at least somewhat coiled shape at rest. In the coiled shape shown in FIG. 4, the length of and the material chosen for the body 112 is such that the body 112, at rest, forms a double circle bracelet bending in an arc extending through approximately 720 degrees. However, it will be appreciated that the body 112 need only extend through an arc of greater than 180 degrees to provide some ability to fit on a wrist and resist being pulled off. Thus, in some embodiments, the body 112, at rest defines a circumference that extends through more than a half circle or oval/ellipse (past 180°, preferably 190° and more preferably 200°) to thus fit over a user's wrist and resist removal absent deforming of the body 112. By making body 112 of a generally pliable material, body 112 can be deformed to change its size or shape, allowing a user to slide dispenser 110 over her hand or wrist.

Thus, a user may wear the dispenser 110 around the wrist. When the user desires to dispense a dose of the product from the dispenser 110, the user removes dispenser 110 from the wrist, and actuates dispenser 110 by pressing movable dispensing tip 134. After the desired amount of product has been dispensed, the user may reposition the dispenser 110 over the wrist to go back to wearing the dispenser 110.

Though various materials will be found to be suitable, in one or more embodiments, the body 12 is formed of a plastic material with elastomeric flex properties. Non-limiting examples include polyvinylchloride (PVC), vinyl, polyethylene (PE), silicone, polybutylene, and polyurethane. In one or more embodiments, the material of the body 12 is chosen to have a Durometer Shore A hardness in the range of from 30 to 100.

Figure 5:
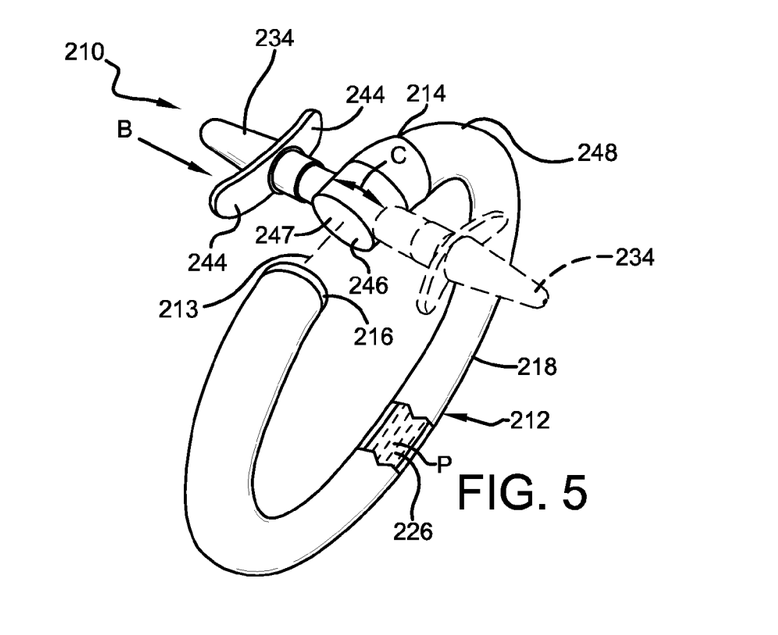
FIG. 5 is a perspective view of a third embodiment of a wearable dispenser in accordance with this invention.

Turning now to FIG. 5, a third dispenser is shown and is generally indicated by the numeral 210. The dispenser 210 includes a body 212 extending from a first end 214 to a second end 216. The body 212 is shown generally in the shape of a loop, but is incomplete, extending through an arc of approximately 320 degrees. As mentioned with respect to the embodiment of FIGS. 3 and 4, the body 212 need only extend through an arc of greater than 180 degrees to provide some ability to fit on a wrist and resist being pulled off. The materials for the body 212 may be the same as those disclosed for the embodiment of FIGS. 3 and 4, having a generally preformed pliable nature.

Though this embodiment shows a body 212 that is cylindrical in cross section, having a cylindrically-shaped sidewall 218, it will be appreciated that practice of this invention does not depend thereon, and other cross-sectional shapes can be employed, as may be desired for a given aesthetic or functional effect. The body 212 is formed of one or more sidewalls 218 and is thereby generally hollow as it extends from the first end 214 to the second end 216, much like the embodiment of FIGS. 3 and 4. In the particular embodiment shown, the body 212 does not include a partition (as at partition 22 of the dispenser 10), because the specific embodiment shown is not intended to join end-to-end. However, it should be appreciated that a partition could be employed to create a connection space, and an axial length could be added to the pump assembly 224 to mate with the connection space substantially as described above with respect to the movable dispensing tip 34 and the connection space 30. That is the end-to-end connecting aspect of the embodiment of FIGS. 1 and 2 could readily be applied to this embodiment, as desired, and specific drawings and additional disclosures are unnecessary for the appreciation of this concept.

In this embodiment, a pump assembly 224 is secured to the opening (not numbered, but similar to opening 20) defined at the first end 214 of the body 212 to thereby close off and define a product space 226 inside of the body 212. The pump assembly 224 may fit partially within the product space 226 or may simply close off the opening at the first end 214, as already described with respect to other embodiments. The product space 226 holds a volume of product that will be dispensed upon proper use of the dispenser 210. In this embodiment, a nasal spray type pump assembly is provided and is associated with a pump housing (not shown, but similar to housing 32) that extends into the product space 226. The pump housing 232, may include a dip tube or other structure to facilitate fluid communication between the product in the product space 226 and the product chamber of the pump assembly 224 (the product chamber is not shown, but is similar to product chamber 35) so that product can be drawn into the pump assembly 224 and dispensed upon reciprocal motion of a movable dispensing tip 234 of the pump assembly 224.

The movable dispensing tip 234 is a nasal spray-type tip, wherein pressing the tip 234 in the direction of arrow B, by means of the two finger rests 244, causes dispensing of product, and releasing the tip 234 after pressing it in this manner causes it to return in the direction opposite arrow B, thereby drawing a dose of product from the product space 226 into the holding chamber for subsequent dispensing. Notably, in the particular embodiment shown, the movable dispensing tip 234 extends from a rotating cap 246 that can rotate relative to a stationary base 248. The rotating cap 246 rotates about the axis 213 of the body 212 at the first end 214, as at arrow C, and the movable dispensing tip 234 extends perpendicularly to that axis. This permits the movable dispensing tip 234 to be rotated to direct the outlet 236 toward a user's hand while the body 212 is still worn as a bracelet on the user's wrist. In such a position, the user can actuate the pump assembly 224 by pressing the movable dispensing tip 234 in the direction of arrow B, thus dispensing a dose of product on his or her hand. The dispenser device 210 does not need to be removed from the user's wrist in order to be used, but of course, it may be. The movable dispensing tip 234 may extend perpendicularly or at other angles off a parallel to the axis 213.

Figure 6:
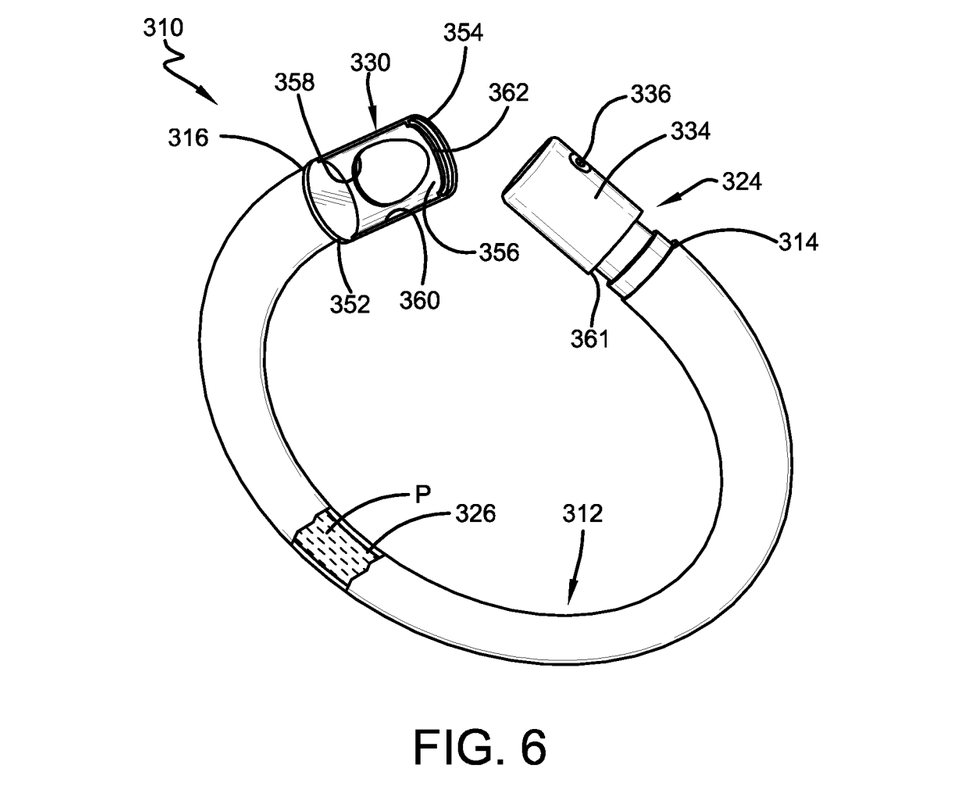
FIG. 6 is a perspective view of a alternative concept for joining wearable dispensers in accordance with this invention in an end-to-end arrangement.
Figure 7:
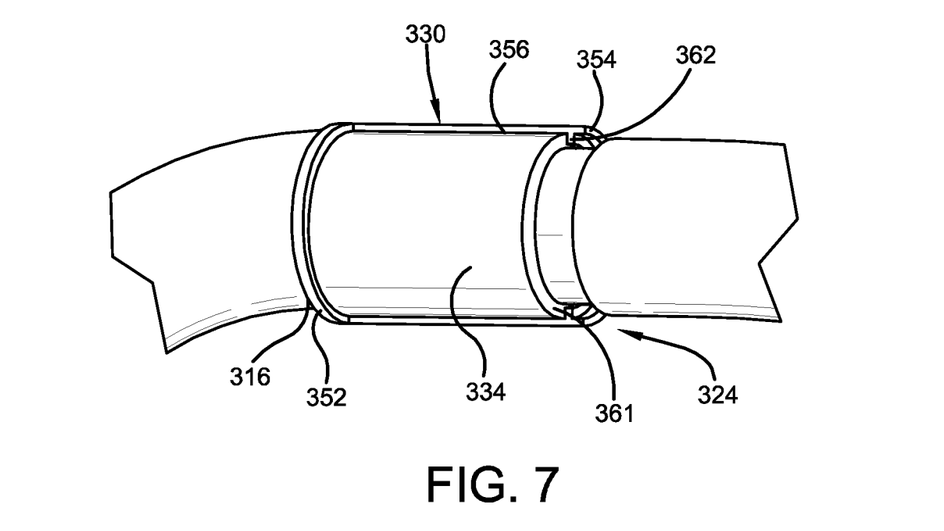
FIG. 7 provides a close-up view of the end-to-end connection of FIG. 6.

Any of the forgoing embodiments can be made to secure end-to-end by incorporation of a connection space at one end to interact with a portion of or extension of a pump assembly at the other end. For example the rotating cap 246 could have an axial extension beyond its distal end 247 that could fit into a connection space defined at the second end 216. In FIGS. 6 and 7, a different structure is shown for securing dispensing devices of this invention in an end-to-end fashion. Notable this concept could be employed with any of the dispensing devices disclosed herein. In the dispensing device 310 of FIGS. 6 and 7, a body 312 extends from a first end 314 to a second end 316, and a product space 326 is defined inside of the body 312 and holds product to be dispensed. A pump assembly 324 communicates with the product in the product space 326 by being secured at the first end 314, and it includes a movable dispensing tip 334 that operates like in previously disclosed pump assemblies (i.e., reciprocal movement causes dispensing and the drawing in of product from the product space 326). The pump assembly 324 may include a dip tube (not shown) or other structure to facilitate fluid communication between pump assembly 324 and the product.

A catch 330 extends from the second end 316 to receive the movable dispensing tip 334. In this particular embodiment, the catch 330 has a generally cylindrical shape and extends from a first end 352 proximate the body 312 to a second open end 354. The catch 330 is formed of a generally cylindrically shaped wall 356 that includes a wall opening 358. The wall 356 also defines a circumferential opening 360, and a circumferential rib 362 extends inwardly from the radial surface of the wall 356 proximate second end 354, and is positioned a distance from first end 352 approximately equal to the axial length of the movable dispensing tip 334. The body 312 is preferably constructed of a generally pliable material, as already described with respect to previous embodiments, so that the body 312 can be bent to place the movable dispensing tip 334 within the catch 330 to create a bracelet. The catch 330 is made of a somewhat rigid yet resilient material such that the movable dispensing tip 334 is simply forced, in a radial direction, through the circumferential opening 360, which gives to the pressure so that the wall 356 of the catch snaps over the movable dispensing tip 334 to hold it. Because the distance between the first end 352 and the rib 362 is approximately equal to the axial length of the movable dispensing tip 334, the tip 334 is securely held without slippage. The rib 362 catches an underside 361 of movable dispensing tip 334, as shown, and the movable dispensing tip 334 is therefore held in snug contact between the first end 352 and the rib 362 of the catch 330. Optionally, the outlet 336 may be aligned with the wall opening 358 such that the pump assembly could be actuated to dispense product through the wall opening 358. However, this is not necessary, as the dispensing device 310 will likely be used after disengaging the movable dispensing tip 334 from the catch 330. The removal can be achieved by inserting one's finger into the wall opening 358 to force the movable dispensing tip 334 out of the catch 330.

In the embodiments described above, the product chamber of the pump assemblies fluidly communicate with the product spaces, either through a short dip tube or otherwise, perhaps through a simple aperture and appropriate valves. Again, suitable pump assemblies and their operation are well known. The bodies of the dispensing devices are made of a suitably flexible material that can bend through the desired degrees or are preformed to a bent bracelet-like shape, and these materials are otherwise generally rigid such that the internal product space does not collapse under the vacuum drawn at the product chamber of the pump assemblies as discussed above. It will be appreciated by those of ordinary skill that the product space will therefore need to be vented in order that air may replace the doses of product drawn into and dispensed out of the product chamber. Otherwise, the pump assemblies will eventually bind up, because they will not be able to draw a large enough vacuum to remove further product from the product space. When vented, as at vent 42 (FIG. 1), the product space will eventually contain air, and will contain enough air that one must properly orient the dispenser to ensure that the pump assembly pulls in product and not air to the product chamber. Particularly, the dispenser must be oriented so that the product P (and not air) directly communicates with the inlet to the product chamber, for example a dip tube, when the volume of the product chamber is increased to draw a vacuum and pull in product from the product space. This renders these vented dispensing devices somewhat burdensome, though they are nonetheless useful in that they serve a dual function as a piece of apparel and as a dispenser, and are always easily available for use.

Any of the embodiments disclosed above could benefit from avoiding the need to vent the product space such that vented air comes into contact with the product. Various concepts for avoiding contact between the product and air are shown and disclosed with reference to FIGS. 8-12. In general, these concepts provide for a collapsing product space. A bellows product space concept is shown in FIGS. 8-10 and is first disclosed.

Figure 8:
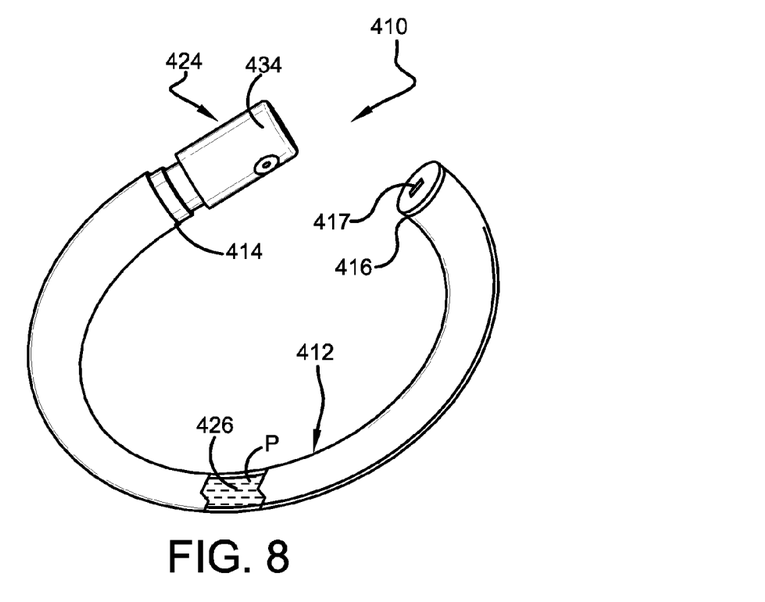
FIG. 8 is a perspective view of a wearable dispenser embodiment in accordance with this invention wherein the wearable dispenser does not need to be vented to allow air to replace product that is dispensed.

A dispensing device 410 is shown in FIG. 8. It is substantially identical to the dispenser of FIG. 4, though it includes a body 412 that does not wrap twice around a wrist. The dispensing device 410 includes a body 412 extending from a first end 414 to a second end 416. In this particular embodiment, the body 412 is preformed to be generally coiled at rest and fit around a user's wrist, but it should be appreciated that the body 412 could instead be a flexible body as in the body 12 of the embodiment of FIG. 1. Indeed, dispenser 410 is disclosed specifically to focus on a bellows chamber that communicates with the pump assembly 424, and the bellows chamber concept can be employed in any of the previous dispenser embodiments disclosed herein.

In this embodiment, the pump assembly 424 communicates with a bellows chamber 460 that is shaped to fit within the body 412. Thus, the bellows chamber 460 provides the product space 426 and holds the product that is to be dispensed. The bellows chamber 460 occupies the expanded configuration shown in FIG. 9 because the product space 426 (i.e., the interior of the bellows chamber 460) is filled with product. As the movable dispensing tip 434 of the pump assembly 424 is pressed and released (i.e., reciprocated) to dispense product and draw product into the pump assembly 424, the bellows chamber 460 collapses. A vent 417 is provided at the second end 416 so that air can enter the body 412 to fill the space no longer occupied by the bellows chamber 460 due to its collapsing. More particularly, as a dose of a product is drawn out of the bellows chamber 460, the bellows chamber 460 collapses in an amount substantially equal to the volume of that dose of product. Eventually, the bellows chamber 460 fully collapses to the fully collapsed configuration of FIG. 10. At this point, it is difficult for any additional product to be drawn into the pump assembly 424 because the volume of product space 426 defined by the bellows chamber 460 cannot shrink any further. Because the bellows structure decreases in size as product is removed therefrom, the product is maintained at the inlet to the pump assembly 424, ensuring that product is always drawn into the pump assembly 424.

Figure 9:
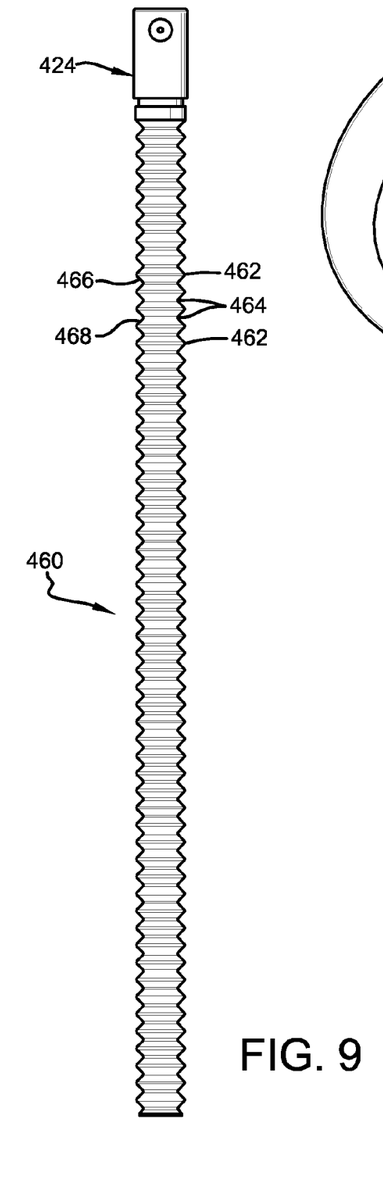
FIG. 9 is a side elevation view of a collapsible bellows for use in any embodiment of this invention in order to avoid the need for venting, the bellows chamber being shown expanded.
Figure 10:
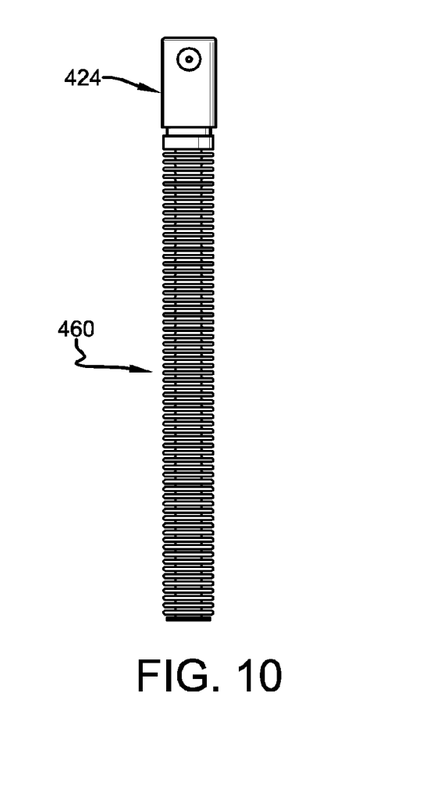
FIG. 10 is a side elevation view of the bellows chamber of FIG. 9, shown collapsed.

The bellows chamber 460 is corrugated, as at ridges 462 and valleys 464, and is made of a material that provides the bellows chamber 460 with the ability to reversibly collapse and extend between the compressed volume (FIG. 10) and the expanded volume (FIG. 9). Considering the bellows chamber 460 from top to bottom in the orientation shown, the corrugated structure is particularly formed by descending conical walls 466 that descend from a given ridge 462 to a valley 464, and ascending conical walls 468 that ascend from a given valley 464 to a neighboring ridge 462. During collapsing, these descending and ascending conical walls, which form a V-shape in an expanded configuration (FIG. 9) lie substantially parallel to each other and abut each other in the collapsed configuration (FIG. 10). In particular embodiments, the pump assembly 424 can be secured to the bellows chamber 460 to form a single unit, herein referred to as "refill unit." Such refill units could be sold to refill the body 412. This would be particularly advantageous in that the user would always be presented with a sterile product inasmuch as the interior of the bellows chamber is not exposed to the air or any other contaminants. Again, it will be appreciated that these concepts could be employed in any of the above embodiments.

It should be appreciated that, as an alternative to the bellows chamber 460, the product could be provided in a collapsible bag formed of a film material. The bag, like the bellows chamber, would collapse as doses of product are drawn therefrom.

Figure 11:
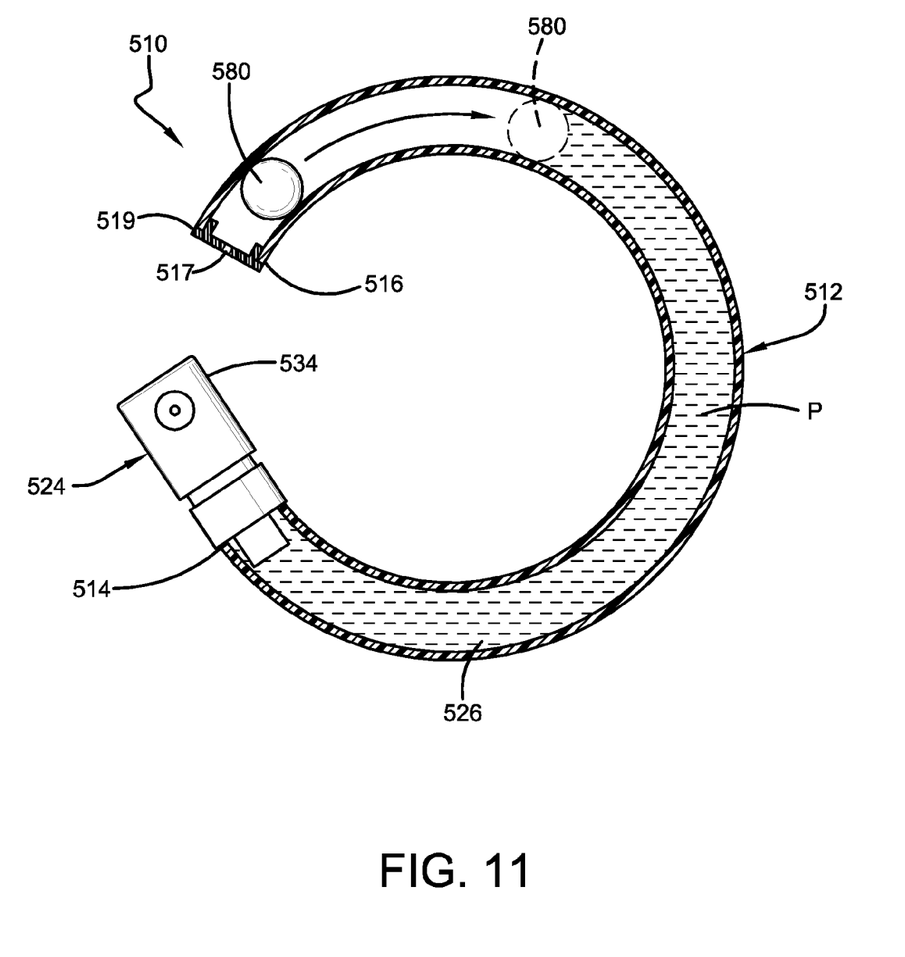
FIG. 11 is a side elevation cross-sectional view of a plug follower concept that could be employed with any embodiment of this invention in order to avoid permitting air to contact the product in the product space.

As an alternative to the bellows chamber and collapsible bag, all of the above embodiments could instead be configured to contact between the product and air by having a plug follower as taught in FIG. 11. This embodiment provides a dispenser identified by the numeral 510. It is substantially identical to the dispenser of FIG. 4, though it is does not have a body 512 shaped to wrap twice around a user's wrist. The dispenser 510 includes a body 512 extending from a first end 514 to a second end 516 and shown in cross section. Though the body 512 is shown preformed to be generally coiled at rest, it could be made to be flexible as in the embodiment of FIG. 1. A pump assembly 524 communicates with the product P in the a product space 526 inside of the body 512. Product is dispensed from the product space 526 by pressing on and releasing the movable dispensing tip 534 of the pump assembly 524. The second end 516 of the body 512 is vented as at vent 517 in a cap 519, and a plug follower 580 is provided in body 512 to accomplish the function of containing the product in the decreasing volume of the product space 526 as product is removed therefrom. Once the pump assembly 524 is actuated to dispense a dose of product and draw a dose of product in from the product space 526, the amount of product within the product space 526 decreases, and the vacuum created thereby draws the plug follower 580 toward the pump assembly 524, as represented by the two different positions for the plug follower 580 in FIG. 11. The plug follower 580 follows the product and continually defines an ever-shrinking product space 526 as doses are dispensed. The plug follower 580 prevents air from entering the product space 526 and ensures that product will always be drawn in by the pump assembly 524. The vent 517 allows air into the body 512, but that air remains behind the plug follow 580 and does not come into contact with the product. The plug follower 580 is shown as a ball, but can be of any shape suitable for intimately contacting the interior wall or walls of the body 512. The plug follower 580 is made of any suitable material that both allows movement of the plug follower 580 within body 512 and reduces or eliminates liquid from leaking past the plug follower 580 where it would introduce air bubbles into the product space 526. Non-limiting examples of material for the plug follower 580 include closed cell foam, open cell foam, rubber, and plastic. In one or more embodiments, the material has a Durometer Shore OO hardness in the range of 20 to 70.

As already disclosed, various aspects of a given embodiment may be combined in whole or in part with aspects of other embodiments. For example any pump assembly structure can be employed with any body type, be it pre-formed (as in FIGS. 4, 5, 6, 8, 11) or formable (FIG. 1). Similarly, the bellows chamber, collapsible bag and plug follower concepts can be employed with any body. Even if pre-formed to mimic a bracelet, the body could still be structured to connect end to end, as seen particularly in FIGS. 6 and 7. Even the dispenser of FIG. 5 could be structured to connect end-to-end by providing the pump assembly thereof with an axial extension and providing the second end of the dispenser with a connection space for that extension. In sum, it should be appreciated that various concepts herein respecting the bodies and the pumps and the refill units and the like can be combined in any combination.

In light of the foregoing, it should be appreciated that the present invention significantly advances the art by providing a wearable dispenser that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A wearable dispenser comprising:
   an elongate body having a first end and a second end and extending from said first end to said second end in an arc forming at least a portion of an ellipse, oval or circle and extending through greater than 180 degrees so as to fit over a wrist;
   a product retained interiorly of said body;
   a pump assembly fluidly communicating with the product in said body, said pump assembly including:
      a movable dispensing tip that, upon reciprocal movement, dispenses a dose of product from the pump assembly and draws another dose of product into the pump assembly, wherein said body defines a product space retaining said product, the wearable dispenser further comprising a plug follower inside said product space, wherein, upon reciprocal movement, said movable dispensing tip dispenses a dose of product from the pump assembly and draws another dose of product into the pump assembly from said product space, the vacuum created thereby drawing the plug follower toward said pump assembly, said plug follower keeping said product isolated from air.

2. The wearable dispenser of claim 1, wherein said second end of said body provides a connection space, wherein said body is formed of a flexible material, wherein said body extends from said first end to said second end in an arc forming at least one ellipse, oval or circle, and wherein at least a portion of said movable dispensing tip of said pump assembly is received in said connection space.

3. The wearable dispenser of claim 1, further comprising a catch at said second end of said body, wherein said body is formed of a flexible material, wherein said body extends from said first end to said second end in an arc forming at least one ellipse, oval or circle, and wherein at least a portion of said movable dispensing tip of said pump assembly is received in said catch.

4. The wearable dispenser of claim 1, wherein said body is formed of a resilient material that maintains said arc at rest, said resilient material yielding to a user's wrist in placing the dispenser on or removing the dispenser from a wrist.

5. The wearable dispenser of claim 3, wherein said body extends from said first end to said second end in an arc forming at least one ellipse, oval or circle.

6. The wearable dispenser of claim 1, wherein said pump assembly includes:
   a base secured to said body, and
   a rotating cap, said movable dispensing tip extending from said rotating cap.

7. The wearable dispenser of claim 6, wherein said movable dispensing tip extends from said rotating cap such that it extends perpendicularly to the axis of said body.

* * * * *